United States Patent [19]

Kao et al.

[11] Patent Number: 5,416,086

[45] Date of Patent: May 16, 1995

[54] RAPAMYCIN 31-ESTER WITH N,N-DIMETHYLGLYCINE DERIVATIVES USEFUL AS IMMUNOSUPPRESSIVE AGENTS

[75] Inventors: Wenling Kao, Paoli, Pa.; Robert L. Vogel, Stratford, N.J.

[73] Assignee: American Home Products Corporation, Madison, N.J.

[21] Appl. No.: 231,557

[22] Filed: Apr. 22, 1994

Related U.S. Application Data

[60] Division of Ser. No. 58,918, May 6, 1993, Pat. No. 5,349,060, which is a continuation-in-part of Ser. No. 1,359, Jan. 7, 1993, abandoned.

[51] Int. Cl.[6] .................. A61K 31/395; C07D 491/16
[52] U.S. Cl. ............................ 514/291; 540/456
[58] Field of Search ........................... 514/291

[56] References Cited

U.S. PATENT DOCUMENTS 5,262,423 11/1993 Kao ............................. 514/291

*Primary Examiner*—Robert T. Bond
*Attorney, Agent, or Firm*—Robert F. Boswell, Jr.

[57] ABSTRACT

A derivative of rapamycin of general formula (1) and (2)

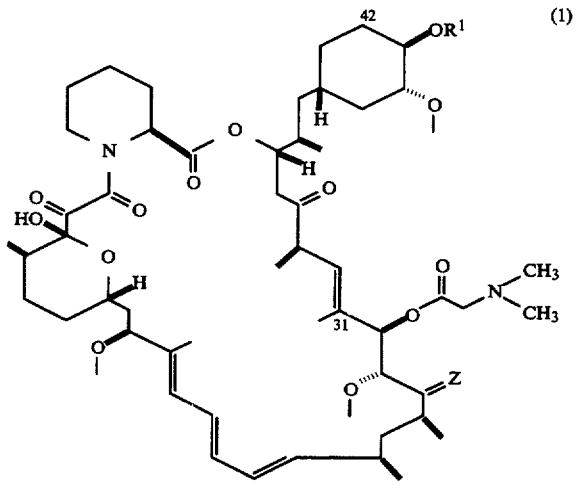

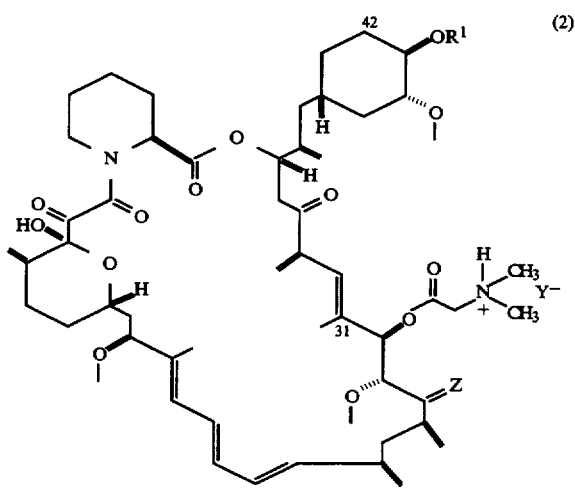

wherein (Abstract continued on next page.)

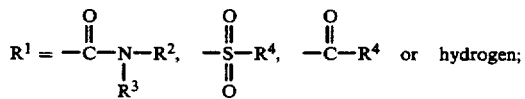

$R^2$ = hydrogen, or lower alkyl having 1 to 6 carbon atoms;

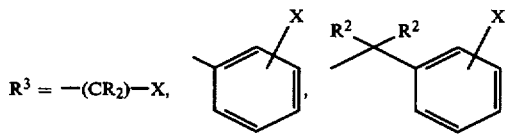

wherein

X = hydrogen, lower alkyl having 1 to 6 carbon atoms, $-CF_3$, $-NO_2$, $-OR^2$, $NR^2$, $SR^2$, or halogen;

$R^4$ = lower alkyl, alkenyl or alkynyl having 1 to 6 carbon atoms or an aromatic or heterocyclic moiety selected from the group consisting of phenyl, naphthyl, thiophenyl and quinolinyl;

$Y^-$ = halide, methanesulfonate, toluene sulfonate or maleate: and

Z = oxygen or OH and H.

which by virtue of its immunosuppressive activity is useful in treating transplantation rejection, host versus graft disease, autoimmune diseases, and diseases of inflammation.

1 Claim, No Drawings

RAPAMYCIN 31-ESTER WITH N,N-DIMETHYLGLYCINE DERIVATIVES USEFUL AS IMMUNOSUPPRESSIVE AGENTS

This is a division of application Ser. No. 08/058,918, filed May 6, 1993, now U.S. Pat. No. 5,349,060, which is a continuation-in-part application of application U.S. Ser. No. 08/001,359, filed Jan. 7, 1993, now abandoned.

BACKGROUND OF THE INVENTION

This invention relates to C-42 carbamates, sulfonates or esters of rapamycin 31-ester with N,N-dimethylglycine, which are useful as immunosuppressive, antiinflammatory, and antifungal agents.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28,727 (1975); H. A. Baker et al., J. Antibiot. 31, 539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1976)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin therefore is also useful in preventing transplant rejection [FASEB 3, 3411 (1989); FASEB 3, 5256 (1989); and R. Y. Calne et al., Lancet 1183 (1978)].

Mono- and diacylated derivatives of rapamycin have been shown to be useful as antifungal agents (U.S. Pat. No. 4,316,885) and used to make water soluble prodrugs of rapamycin (U.S. Pat. No. 4,650,803). U.S. Pat. No. 4,650,803 discloses water soluble mono- and di-aminoalkanoyl prodrugs of rapamycin. Recently, the numbering convention for rapamycin has been changed; therefore according to Chemical Abstracts nomenclature, the esters described above would be at the 31- and 42- positions.

DESCRIPTION OF THE INVENTION

This invention relates to C-42 carbamates, sulfonates or esters of rapamycin 31-ester with N,N-dimethylglycine of general formula (I)

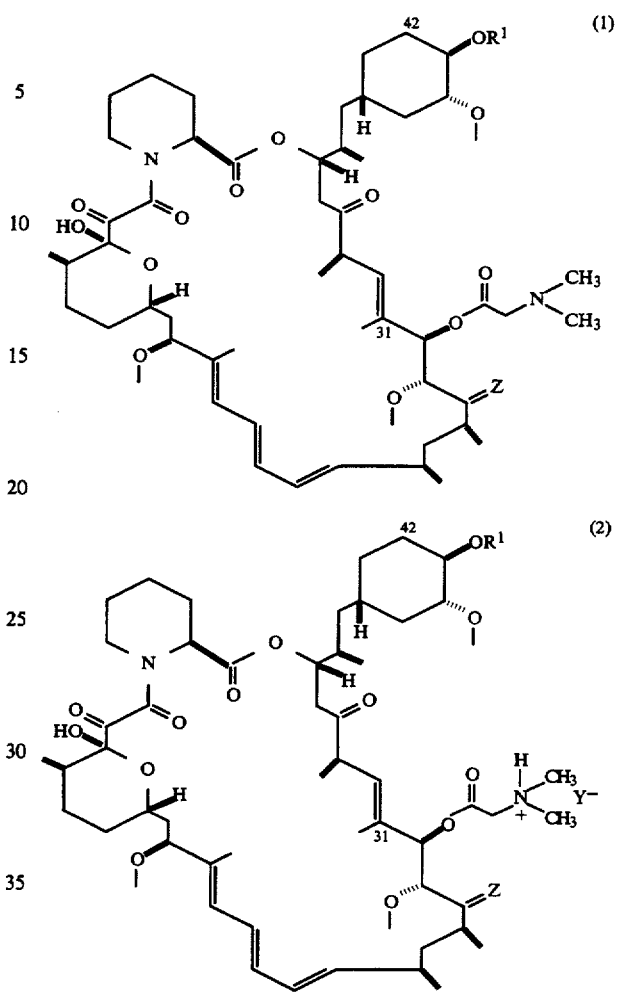

wherein

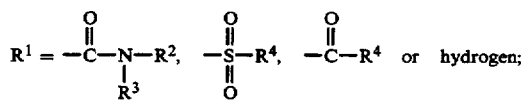

$R^2$=hydrogen, or lower alkyl having 1 to 6 carbon atoms;

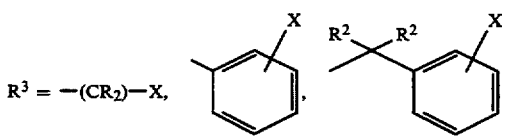

wherein X=hydrogen, lower alkyl having 1 to 6 carbon atoms, —$CF_3$, —$NO_2$, —$OR^2$, $NR^2$, $SR^2$, or halogen;

$R^4$=lower alkyl, alkenyl, or alkynyl having 1 to 6 carbon atoms or an aromatic or heterocyclic moiety selected from the group consisting of phenyl, naphthyl, thiophenyl and quinolinyl;

$Y^-$=halide, methanesulfonate, toluene sulfonate or maleate; and

Z=oxygen or OH and H

The C-42 carbamates, sulfonates or esters of rapamycin 31-ester with N,N-dimethylglycine, of this invention can be prepared by the standard literature procedure as outlined below:

$$R^5-OH + O=C=N-R^6 \longrightarrow R^5-O-\overset{O}{\underset{\|}{C}}-NH-R^6$$

$$R^5-OH + Cl-\overset{O}{\underset{\underset{O}{\|}}{\overset{\|}{S}}}-R^6 \longrightarrow R^5-O-\overset{O}{\underset{\underset{O}{\|}}{\overset{\|}{S}}}-R^6$$

$$R^5-OH + R^6-\overset{O}{\underset{\|}{C}}-O-\overset{O}{\underset{\|}{C}}-R^6 \longrightarrow R^5-O-\overset{O}{\underset{\|}{C}}-R^6$$

$$\underset{29}{-\overset{O}{\underset{\|}{C}}-} \longrightarrow \underset{29}{-\overset{OH}{\underset{|}{CH}}-}$$

wherein $R^5$—OH is the hydroxy group at the 42-position of rapamycin; $R^6$ is $R^2$ or $R^3$ or $R^4$ wherein $R^2$, $R^3$ and $R^4$ are as defined above: and $$\underset{29}{-\overset{O}{\underset{\|}{C}}-}$$

is the carbonyl group at the 29-position of rapamycin.

The carbamate and sulfonate formations of rapamycin have been described in patent applications (U.S. Ser. Nos. 07/686,728, filed Apr. 17, 1991 and 07/846,637, filed Mar. 5, 1992). The ester formation between alcohol and anhydride has been described [John McMurry, Organic Chemistry, 2nd edition, 1988, page 758]. Sodium triacetoxyborohydride reduction of ketone was reported in Chemical Communications 535 (1975). The pharmaceutically acceptable salts may be formed from amine and Lewis acid, which are also documented [John McMurry, Organic Chemistry, 2nd edition, 1988, page 899].

PRIOR ART

Compounds of this invention differ from compounds described in U.S. Ser. Nos. 07/686,728, filed Apr. 17, 1991 and 07/846,637, filed Mar. 5, 1992 in having a dimethyl glycinate moiety at the 31-position of rapamycin.

The following examples illustrate the preparation of representative compounds of this invention.

EXAMPLE 1

Rapamycin 31-ester with N,N-dimethylglycine HCl salt 42-ester with p-toluenesulfonic acid A solution of 200 mg of rapamycin 31-ester with N,N-dimethylglycine (made by the procedure of U.S. Pat. No. 4,650,803) in one mL of pyridine was treated at room temperature with 114 mg of para-toluenesulfonyl chloride. After stirring at room temperature for 24 hours, the reaction mixture was diluted with 15 mL of ice-cold 1N HCl and extracted with ethyl acetate. The ethyl acetate extract was washed with brine, dried with magnesium sulfate and evaporated. The residue was chromatographed on silica gel. Elution with ethyl acetate:hexane=1:1 solvent system afforded 165 mg of rapamycin 42-tosylate, 31-(N,N-dimethyl)glycinate as a white foam.

NMR (CDCl$_3$, 200 MHz), 7.82 (d, J=10 CPS, 2H, aromatic proton ortho to sulfonyl function), 7.35 (d, J=10 CPS, 2H, aromatic proton meta to sulfonyl function), 3.36 (s, 3H, OCH$_3$), 3.18 (s, 6H, two OCH$_3$), 2.46 (s, 3H, aromatic —CH$_3$), 2.35 (s, 6H $$-\underset{\underset{CH_3}{|}}{N}-CH_3)$$

The above free amine was dissolved in 5 mL of ether and treated at 0° C. under nitrogen with 1.43 mL of 0.1 M HCl in ether. The white crystalline material was collected by filtration, and dried at room temperature in vacuum for 20 hours to afford 23 mg of the title product as a white solid, mp 120°–123° C.

IR: KBr max 3420 (OH), 2920, 2600–2200

$$\left(-\underset{\underset{CH_3}{|}}{\overset{\overset{CH_3}{|}}{\overset{+}{N}}}-H\ \bar{Cl}\right),$$

1745–1730 (C=O), 1640 (amide C=O), 1350 (—SO$_2$—) NMR (CDCl$_3$, 400 MHz), 7.74 (d, J=10.8, 2H, aromatic proton ortho to sulfonyl function), 7.42 (d, J=10.2, 2H, aromatic proton meta to sulfonyl function), 3.32 (s, 6H, $$-\underset{\underset{CH_3}{|}}{\overset{\overset{H}{|}}{\overset{+}{N}}}-CH_3),$$

3.18 (s, 3H, OCH$_3$), 3.07 (s, 3H, OCH$_3$), 3.03 (s, 3H, OCH$_3$), 2.39 (s, 3H, aromatic CH$_3$). MS (positive ion FAB): 1153 (MH+ for free base).

EXAMPLE 2

Rapamycin 31-ester with N,N-dimethylglycine HCl salt 42-ester with acetic acid

A solution of 450 mg of rapamycin 31-ester with N,N-dimethylglycine (made by the procedure of U.S. Pat. No. 4,650,803) in 1.8 mL of pyridine was treated at 0° C. under nitrogen with 150 mg of acetic anhydride. After stirring at room temperature for 2 hours, the reaction mixture was diluted with 150 mL of ethyl acetate then washed with brine. The ethyl acetate solution was dried with magnesium sulfate and evaporated. The residue was chromatographed on silica gel. Elution with ethyl acetate afforded 80 mg of rapamycin 42-acetate, 31-ester with N,N-dimethylglycine as a white foam.

The above free amine was dissolved in 5 mL of ether and treated at 0° C. under nitrogen with 0.8 mL of 0.1M HCl in ether. A white crystalline material was formed, collected by filtration and dried at room temperature for 20 hours to afford 32 mg of the title product as a white solid, mp 129°–134° C.

IR: KBr max 3425 (OH), 2930, 2600–2250

$$(-\underset{\underset{CH_3}{|}}{\overset{\overset{H}{|}}{\overset{+}{N}}}-CH_3\ Cl^-),$$

1735 (C=O), 1645 (amide C=O) 1450, 1370, 1240. NMR (CDCl$_3$, 400 MHz), 3.31 (s, 6H, methyl of

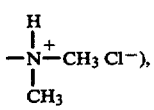

328 (s, 3H, OCH₃), 3.20 (s, 3H, OCH₃), 3.05 (s, 3H, OCH₃), 1.99 (s, 3H,

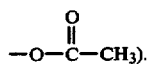

MS (positive FAB); 1013 (M+ for free base). Analysis Calcd for C₅₇H₈₈N₂O₁₅.HCl.H₂O C62.46; H 8.19; N 2.56. Found: C 62.54; H 8.27; N 2.27.

EXAMPLE 3

Rapamycin 31-ester with N,N-dimethylglycine HCl salt 42-ester with phenylcarbamic acid A solution of 500 mg of rapamycin 31-ester with N,N-dimethylglycine (made by the procedure of U.S. Pat. No. 4,650,803) in 2.5 mL of pyridine was treated at 0° C. under nitrogen with 0.4 g of phenyl isocyanate. Stirring at room temperature for 2 hours, the reaction mixture was diluted with 100 mL of ethyl acetate. The ethyl acetate solution was washed with water, dried with magnesium sulfate and evaporated to dryness. The residue was chromatographed on silica gel. Elution with hexane:ethyl acetate=1:3 afforded 96 mg of rapamycin 42-phenyl carbamate, 31-(N,N-dimethyl)-glycinate as a whim foam.

The above amine was dissolved in 6 mL of ether and treated at 0° C. under nitrogen with 0.86 mL of 0.1M HCl in ether. The white crystalline material was collected by filtration, and dried at room temperature under vacuum to afford 52 mg of the title product as a white solid, mp 135°-138° C.

IR KBr max 3400 (OH), 2930, 2500-2200

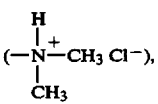

1725 (C=0), (amide C=0), 1605 (aromatic), 1445, 1220, 990. MS (neg. ion FAB): 1117 (M⁻ for free base).

EXAMPLE 4

Rapamycin 31-ester with N,N-dimethylglycine HCl salt 41-ester with 4-fluorophenyl carbamic acid A solution of 500 mg of rapamycin 31-ester with N,N-dimethylglycine (made by the procedure of U.S. Pat. No. 4,650,803) in 4 mL of pyridine was treated at 0° C. under nitrogen with 137 mg of 4-fluorophenyl isocyanate. Stirring at room temperature for 18 hours, the mixture was diluted with 25 mL of brine and extracted with ethyl acetate (3×50 mL). The ethyl acetate solution was washed with water, dried with magnesium sulfate and evaporated to dryness. The residue was mixed with 20 mL of ether and stirred at room temperature for 10 minutes. The resulting suspension was filtered. The clear ether filtrate was cooled to 0° C. under nitrogen and treated with 0.5 mL of 1N HCl in ether to form the hydrochloride salt. The crystalline salt was collected and dried at 54° C. under vacuum for 20 hours to afford 370 mg of the title product as a white powder, mp 125°-130° C.

IR KBr max 3430 (OH), 2940, 2600-2350

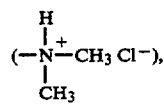

1720 (C=0), 1645 (amide C=0), 1620 (aromatic), 1510, 1210, 990. NMR (CDCl₃, 400 MHz), 7.45 (m, 2H, aromatic protons ortho to fluorine group), 7.10 (m, 2H, aromatic protons meta to fluorine group), 3.60 (s, 3H, OCH₃), 3.20 (s, 3H, OCH₃), 3.04 (s, 3H, OCH₃), 2.80 (s, 6H, methyl of

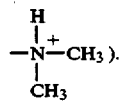

MS (positive ion FAB): 1136 (MH+ for free base).

EXAMPLE 5

Rapamycin 31-ester with N,N-dimethylglycine HCl salt 42-ester with phenylsulfonyl carbamic acid A solution of 200 mg of rapamycin 31-ester with N,N-dimethylglycine (made by the procedure of U.S. Pat. No. 4,650,803) in one mL of dichloromethane was treated at 0° C. under nitrogen with 74 mg of phenylsulfonyl isocyanate. After stirring at 0° C. under nitrogen for 6 hours, the mixture was diluted with 60 mL of dichloromethane, washed with water and dried with magnesium sulfate. The dicholoromethane solution was evaporated to dryness and the residue was treated with 1.5 mL of ether and 1.0 mL of ethyl acetate. To this solution at −10° C., 0.3 mL of 1M HCl in ether was added. After stirring at −10° C. under nitrogen for 10 minutes, the mixture was evaporated to dryness and the residue was triturated with 15 mL of ether. The resulting suspension was filtered and the solid material collected and dried at 54° C. under vacuum for 20 hours to afford 130 mg of the title product as a pale solid, mp 122°-126° C.

IR KBr max 3400 (OH), 2930, 2700-2300

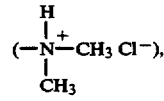

1745 (C=0), 1640 (amide C=0), 1450, 1350 (—SO₂—), 1160 (—SO₂—), 1080, 980. H¹NMR (CDCl₃, 400 MHz), 7.80 (m, 2H, aromatic protons ortho to SO₂ group), 7.56 (m, 3H, aromatic protons meta and para to SO₂ group), 3.13 (s, 3H, OCH₃), 3.11 (s, 3H, OCH₃), 3.02 (s, 3H, OCH₃), 2.78 (s, 6H, methyl of

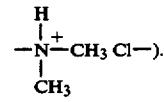

MS (positive ion FAB): 1182 (MH+ for free base).

EXAMPLE 6

33-Deoxy-33-hydroxyrapamycin 31-ester with N,N-dimethylglycine HCl salt

A solution of 1.0 g of rapamycin 31-(N,N-dimethyl)-glycinate (made by the procedure of U.S. Pat. No. 4,650,803) in 17 mL of tetrahydrofuran was treated at 0° C. under nitrogen with 1.28 g of sodium triacetoxyborohydride and 3.0 mL of acetic acid. Stirring at room temperature for 4 hours, the reaction mixture was diluted with 25 mL of brine and extracted with ethyl acetate (3×40 mL). The ethyl acetate solution was washed with brine, dried with magnesium sulfate and evaporated. The residue was triturated with ether (2×5 mL) and the resulting solid material was dissolved in a mixture of 3 mL dichloromethane −2 mL ether. The clear solution was treated at 0° C. with 0.6 mL of 1N HCl in ether. After stirring for 10 minutes, the solution was evaporated to dryness. The resulting foam was triturated with ether (4×5 mL) and dried in vacuum to afford 430 mg of the tire product as a yellow powder, mp 115°–118° C.

IR KBr max 3430 (OH), 2930, 2700–2300

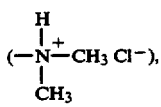

1750 (C=O), 1645 (amide C=O), 1460, 1380, 1215, 1100, 990. NMR (CDCl3, 400 MHz), 3.29 (s, 3H, OCH3), 3.25 (s, 3H, OCH3), 3.17 (s, 3H, OCH3), 2.80 (s, 6H, methyl of

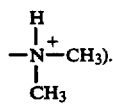

MS (positive ion FAB): 1001 (MH+ for free base).

EXAMPLE 7

Rapamycin 31-ester with N,N-dimethylglycine 42-ester with 8-quinolinesulfonic acid A solution of 0.50 g rapamycin 31-ester with N,N-dimethylglycine and 0.42 g 8-quinolinesulfonyl chloride in 20 mL dry pyridine was stirred at 22° C. for 90 hours. The pyridine was pumped off and the residue partitioned between water and ethyl acetate. The organic portion was dried over MgSO4, stripped of solvent and flash chromatographed through silica gel using ethyl acetate to yield 120 mg of nearly white solid, mp 110°–117° C.

IR (KBr): 3430, 2920, 1730, 1640, 1450, 1170, 788 and 670 cm$^{-1}$. NMR (CDCl3, 400 MHz): 3.32 (s, 3H, OMe), 3.14 (s, 3H, OMe), 2.62 (s, 3H, OMe), 2.30 (s, 6H,

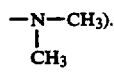

MS (neg FAB): 1189 (M−), 997.

EXAMPLE 8

Rapamycin 31-ester with N,N-dimethylglycine 42-ester with 5-(dimethylamino)naphthalene-1-sulfonic acid To a solution of 2.3 g rapamycin 42-ester with 5-(dimethylamino)naphthalene-1-sulfonic acid in 25 mL methylene chloride were added 0.32 g N,N-dimethylglycine, 0.77 g 1-(3-dimethylaminopropyl)-3-ethylcarbodiimide hydrochloride and 60 mg 4dimethylaminopyridine. After stirring 72 hours at 22° C., the reaction mixture was diluted with methylene chloride, washed with water and brine, dried over MgSO4 and evaporated to a yellow solid foam. Chromatography through silica gel using methylene chloride with methanol concentrations increasing from 0.5% to 2% yielded 130 mg pure product as a yellow solid, mp 100°–110° C.

IR (KBr): 3430 (OH), 2930, 1730, 1645, 1450, 1160, 788 and 632 cm$^{-1}$. NMR (CDCl3, 400 MHz): 3.23 (s, 3H, OMe); 3.05 (s, 3H, OMe); 2.80 (s, 6H, NMe2); 2.65 (s, 3H, OMe); 2.22 (s, 6H, NMe2). MS (neg FAB): 1231 (M−), 998.

EXAMPLE 9

Rapamycin 31-ester with N,N-dimethylglycine 42-ester with D-(+)-10-camphorsulfonic acid A solution of 0.50 g rapamycin 31-ester with N,N-dimethylglycine (made by the procedure of U.S. Pat. No. 4,650,803) and 0.40 g D-(+)-10-camphorsulfonyl chloride in 20 mL pyridine was stirred at 22° C. for 66 hours. The pyridine was removed under vacuum and the residue partitioned between water and ethyl acetate. The organic portion was dried over MgSO4, evaporated to dryness and flash chromatographed through silica gel using ethyl acetate, yielding 0.44 g product as a pale yellow solid, mp 116°–119° C.

IR (KBr): 3430, 2930, 1740, 1645, 1450, 1365, 985 and 965 cm$^{-1}$. NMR (CDCl3, 400 MHz): 3.41 (s, 3H, OMe), 3.33 (s, 3H, OMe), 3.15 (s, 3H, OMe), 2.32 (s, $$-\underset{\underset{CH_3}{|}}{N}-CH_3),$$

1.13 (s, 3H, camphor CH3), 0.89 (s, 3H, camphor CH3). MS (neg FAB): 1212 (M−), 997.

BIOLOGICAL DATA

The comitogen-induced thymocyte proliferation procedure (LAF) was used as an in vitro measure of the immunosuppressive effects of representative compounds. Briefly, cells from the thymus of normal BALB/c mice were cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls.

The second in vivo test procedure is designed to determine the survival time of pinch skin graft from male BALB/c donors transplanted to male C3H recipients. The method is adapted from Billingham R. E. and Medawar P. B., J. Exp. Biol. 28:385–402, (1951). Briefly, a pinch skin graft from the donor is grafted on the dorsum of the recipient as an allograft and an isograft is used as control in the same region. The recipients are treated with the test compound, intraperitoneally once daily for 6 consecutive days. Untreated recipients serve as rejection control. The graft is monitored daily and observations are recorded until the graft becomes 95% area necrosis or the suture line is off. This is considered as the rejection day. The graft survival time is one day before the rejection day. The mean graft survival time (number of days±S.D.) of the drug treatment group is compared with the control group.

The following table summarizes the results of representative compounds of this invention in these two standard test procedures.

TABLE 1

Biological Activity
Percentage Inhibition in LAF Assay

| Example | at 100 nM concentration | | at 10 nM concentration | | Skin Graft Assay days ± SD |
|---|---|---|---|---|---|
| | Analogs | Rapamycin | Analogs | Rapamycin | Analogs |
| 1 | −74 | −95 | −6 | −90 | — |
| 2 | −96 | −97 | −59 | −96 | — |
| 3 | −82 | −97 | −14 | −89 | — |
| 4 | −94 | −96 | −38 | −84 | 8.17 ± 0.41 |
| 5 | −35 | −96 | 1 | −85 | 10.00 ± 0.57 |
| 6 | −76 | −96 | −13 | −85 | 9.50 ± 1.22 |
| 7 | −94 | −94 | −62 | −89 | 9.33 ± 1.22 |
| 8 | −54 | −95 | 13 | −88 | — |
| 9 | — | — | — | — | — |

The results of these standard pharmacological test procedures demonstrate high immunosuppressive activity both in vitro and in vivo for the compounds of the present invention. A positive ratio in the LAF test procedure indicates suppression of T-cell proliferation. As transplanted pinch skin grafts are typically rejected within 6–7 days without the use of an immunosuppressive agent, the substantial increase in survival time of the skin graft when treated with the compounds of the present invention further demonstrate their utility as immunosuppressive agents.

Based on the results of these standard pharmacological test procedures, the compounds of this invention are useful in the prevention and treatment of transplant rejection such as heart, kidney, liver, bone marrow, and skin transplants; graft versus host disease; autoimmune and proliferative diseases such as, systemic lupus erythematosus, rheumatoid arthritis, type 1 diabetes, multiple sclerosis, glomerular nephritis, Hashimoto's thyroiditis, myastenia gravis, uveitis and psoriasis; diseases of inflammation such as dermatitis, eczema, seborrhea and inflammatory bowel disease; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carder such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. The compound can also be administered orally either in liquid or solid composition form.

Preferably, the pharmaceutical composition is in unit dosage form, e.g., as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

What is claimed is:

1. A method of treating transplantation rejection, host versus graft disease, autoimmune diseases, and diseases of inflammation in a mammal by administering an effective amount of a compound of general formula (1) and (2)

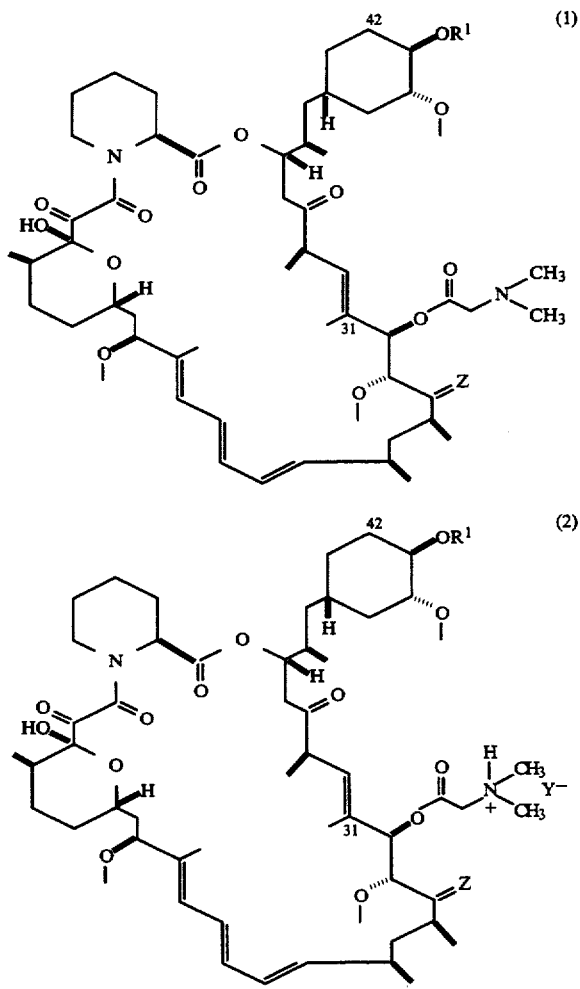

wherein

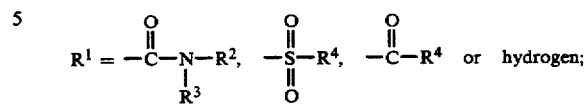

, 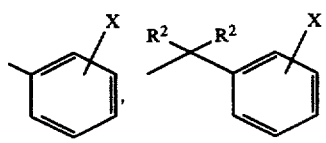

$R^2$ = hydrogen, or lower alkyl having 1 to 6 carbon atoms;

wherein X = hydrogen, lower alkyl having 1 to 6 carbon atoms, —$CF_3$, —$NO_2$, —$OR^2$, $NR^2$, $SR^2$, or halogen;

$R^4$ = lower alkyl, alkenyl or alkynyl having 1 to 6 carbon atoms or an aromatic or heterocyclic moiety selected from the group consisting of phenyl, naphthyl, thiophenyl and quinolinyl;

$Y^-$ = halide, methanesulfonate, toluene sulfonate or maleate; and

Z = oxygen or OH and H.

* * * * *